United States Patent [19]

Isoyama

[11] Patent Number: 5,367,555
[45] Date of Patent: Nov. 22, 1994

[54] MEDICAL DATA REPORTER

[75] Inventor: Takashi Isoyama, Tokyo, Japan

[73] Assignees: Aisin Seiki Kabushiki Kaisha; Kabushiki Kaisha Shinsangyokaihatsu, Japan

[21] Appl. No.: 676,379

[22] Filed: Mar. 28, 1991

[30] Foreign Application Priority Data

Mar. 29, 1990 [JP] Japan .................. 2-82156

[51] Int. Cl.⁵ ........................................ H04M 11/00
[52] U.S. Cl. .......................... 379/38; 379/57; 379/96; 379/106
[58] Field of Search .................... 379/38, 37, 39, 40, 379/42, 45, 56, 57, 58, 96, 106, 107, 102, 104, 105; 340/825.44, 825.45, 825.46; 128/904

[56] References Cited

U.S. PATENT DOCUMENTS

| | | | |
|---|---|---|---|
| 4,273,961 | 6/1981 | Blank et al. | 379/40 |
| 4,337,377 | 6/1982 | Van Riper et al. | 379/38 |
| 4,531,527 | 7/1985 | Reinhold, Jr. et al. | 379/38 |
| 4,839,917 | 6/1989 | Oliver | 379/45 |
| 4,847,892 | 7/1989 | Shelley | 379/107 |
| 4,856,047 | 8/1989 | Saunders | 379/57 |
| 4,924,491 | 5/1990 | Compton et al. | 379/37 |
| 5,010,568 | 4/1991 | Merriam et al. | 379/106 |
| 5,036,852 | 8/1991 | Leishman | 379/38 |

Primary Examiner—Curtis Kuntz
Assistant Examiner—Stella L. Woo
Attorney, Agent, or Firm—Banner, Birch, McKie & Beckett

[57] ABSTRACT

A medical reporting system includes a medical data transmitter that receives medical data from a medical monitoring system. The medical data is then transmitted to a telephone network and received from the telephone network by a remote receiver. The medical data is displayed by the medical data receiver. Further, the medical data receiver may also emit an audible sound to indicate the presence of important data.

11 Claims, 3 Drawing Sheets

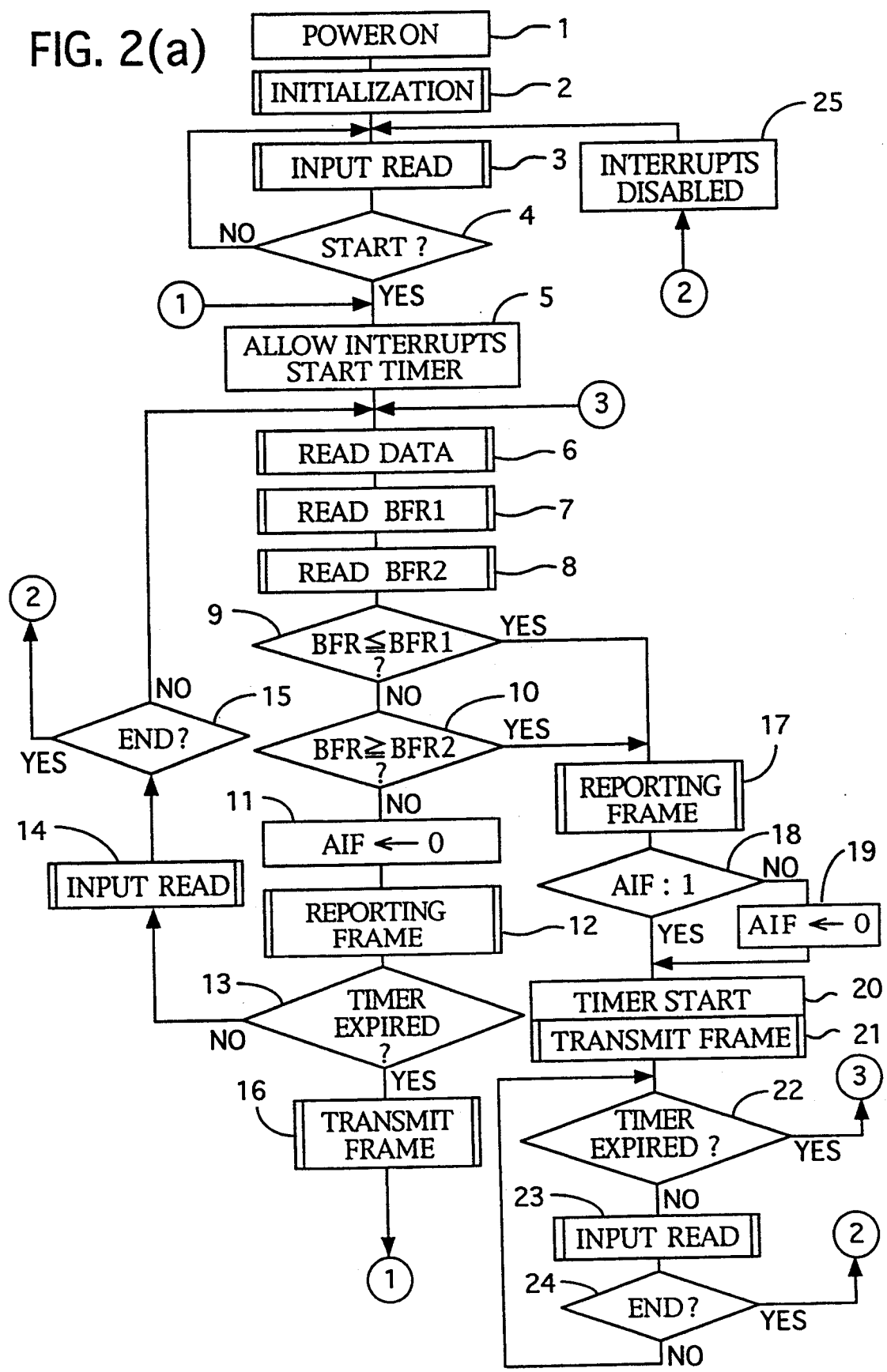

MEDICAL DATA REPORTER

FIELD OF THE INVENTION

The invention is directed to a medical data reporting system for reporting the medical condition and status of a organism connected to a monitoring device.

BACKGROUND OF THE INVENTION

Human beings and other living organisms often require treatment which includes constant monitoring of bodily functions or characteristics, such as blood flow rate (BFR), blood pressure (BP), pulse, electrocardiograms (ECG), respiration cycles, and body temperature. Monitoring of these functions and characteristics takes on special importance when the life of the organism is maintained, at least in part, by a life support system. Common life support systems include, for example, artificial respirators and artificial hearts. These life support systems provide numerous informational outputs describing the condition of the organism to which they are connected. Such outputs may indicate, for example, blood flow rate, blood pressure, heart beat, electrocardiograms, respiration cycles, and body temperature.

Different characteristics and functions may be of special importance depending upon the purpose of the treatment. For example, if the life support system is an artificial heart driver and monitor, blood flow rate has particular importance. It must be constantly monitored to detect any irregularities in the operation of the driver.

Prior art devices provide their data at the treatment site in a form requiring considerable medical expertise and substantial knowledge about the medical apparatus. Therefore, persons with this knowledge typically must constantly monitor the life support system. The requirement that a skilled person must monitor the system or device at the treatment site increases medical costs and tires these workers, thus reducing their efficiency.

SUMMARY OF THE INVENTION

The present invention provides a medical monitoring system which does not require that a highly skilled worker remain with the monitoring equipment at all times. The invention further provides a medical monitoring system that allows accurate and precise medical information to be easily monitored by skilled personnel at all times.

In accordance with the invention, a medical reporting system according to a first aspect of the invention includes a device for gathering data from a medical monitoring device. The monitoring device monitors certain characteristics of a living organism. The data is transmitted to a remote location and displayed. The data is updated at a predetermined interval.

The invention also relates to a medical reporting system comprising a device for gathering and transmitting information as in the first aspect, and further comprises a provision for monitoring at least one biological function, as detected by the monitoring system and determining whether the function is within a predetermined range. If the data is within the predetermined range, the reporting system transmits the data to the remote location to be displayed. It is updated at a predetermined interval. If the data is not within the predetermined range, the data is transmitted and displayed; however, in addition, an alarm is sounded at the remote unit to alert monitoring personnel of an unusual occurrence.

BRIEF DESCRIPTION OF THE DRAWINGS

The invention will best be understood when the following description is read with reference to the appended drawings in which:

FIGS. 2(a) and 2(b) are flow charts describing the operation of the invention.

DETAILED DESCRIPTION OF THE INVENTION

Figure 1:
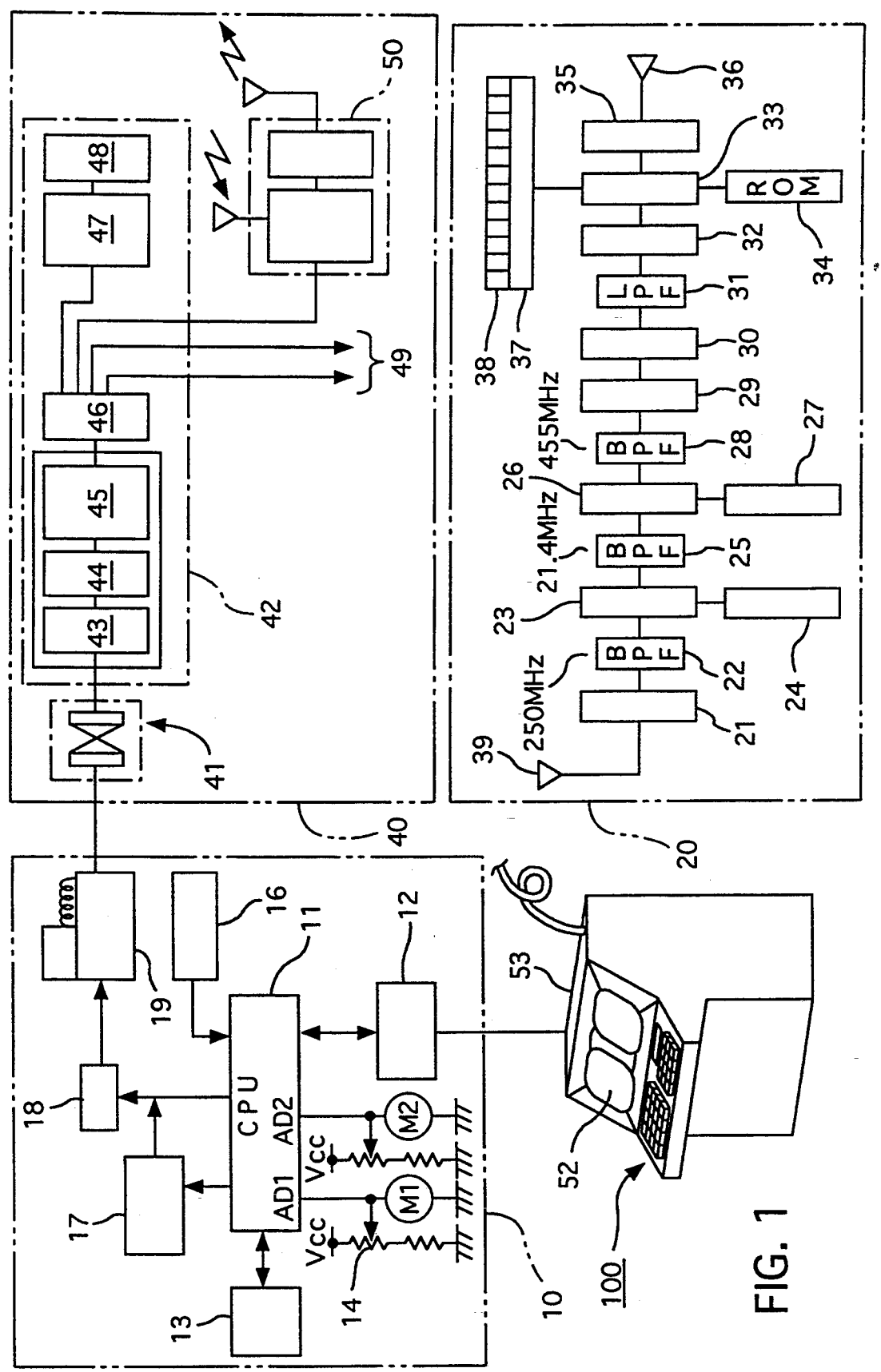
FIG. 1 is a block diagram showing a system in accordance with the invention.

A medical data reporting system is provided for reporting data from a medical monitoring system to a remote location. A system in accordance with the invention will be discussed in reference to FIG. 1. A medical data transmitter 10 is used to transmit medical data from a life support system 100. Medical transmitter 10 includes a CPU or microprocessor 11 that controls the transmitter. The CPU controls the generation, transmission and detection of data. Microprocessor 11 accepts input from potentiometers 14 and 15. The voltage across the potentiometers 14 and 15 is indicative of the minimum and maximum values, respectively, for a selected biological function. Voltmeters $M_1$ and $M_2$ give a visual indication of the voltages across potentiometers 14 and 15, respectively.

A communication interface 12 is interposed between life support system 100 and microprocessor 11. The communication interface 12 provides the needed communication link between life support system 100 and microprocessor 11. A keyboard 13 is provided as part of medical transmitter 10 to allow a user to input commands. A timer 16 inputs timing information to microprocessor 11. Timer 16 is used, for example, to time the intervals at which data is transmitted, as described below.

Data is transmitted from the medical data transmitter 10 to public telephone network 40 by use of elements 17–19 of FIG. 1. Modem 18 and automatic dialer 17 are used to telephone a designated number and transmit information over a telephone line. Automatic dialer 17 and modem 18 are controlled by circuit controller 19 which coordinates their activity.

Preferably, data is transmitted by modem 18 over a public telephone network to a remote location. In a more preferred embodiment, the public telephone network has radio transmission capability. Such technology is widely used today to drive pocket pagers. In these systems, a person wishing to contact or give data to another, who is carrying a pocket pager, dials a telephone number associated with the pager. The telephone network then transmits a signal to the pager, thus causing it to emit an audio signal, display a visual message, or both.

Any suitable public telephone network is used to transmit data from modem 18 to a remote location. A typical telephone network is illustrated at reference numeral 40 in FIG. 1. A typical public telephone network 40 with radio transmission capability includes a connection to an exchange 41. Public telephone network 40 further includes a central station 42 including trunk 43, register 44, subscriber number compiler 45, coder 46, phase compensator 47, and transmitter 48.

Also part of the network are base stations in the area such as base station 50. Those base stations in the area, such as base station 50, may communicate with central station 42 by either radio or wired communication. Additionally, central station 42 may communicate with base stations not in the area by use of wired connections denoted by connection paths 49. The precise design and features of public telephone network 40 form no part of this invention, however.

A medical data receiver 20 is provided for receiving information transmitted by medical data transmitter 10 over public telephone network 40. Skilled practitioners recognize that there exists a number of devices which are capable of receiving radio signals and converting them to display information and provide audio signals. However, the invention is described herein with regard to a particular receiver. Thus, the description is fairly specific with regard to receiver parameters. However, other receivers may utilize different parameters, such as different band pass frequency filter parameters. Skilled practitioners will be able to select such equipment in accordance with the description set forth herein.

A suitable receiver includes an antenna 39 for receiving radio signals and inputting them to a high frequency amplification circuit 21. The output of the amplification circuit 21 is input to a first band pass filter 22. First bandpass filter 22 has a center frequency of 250 MHz. The output of first bandpass filter 22 is input to first mixer 23. First mixer 23 also accepts input from first local dispatch 24 and provides its output to second bandpass filter 25. Second bandpass filter 25 has a center frequency of 21.4 MHz. Second bandpass filter 25 provides its output to second mixer 26. Mixer 26 accepts also accepts input from second local dispatch 27 and provides output to third band pass filter 28. Third band pass filter 28 has a center frequency of 455 kHz. The output of third band pass filter 28 is then amplified by medium frequency amplification circuit 29 and passed to frequency discriminator 30. The signal leaving frequency discriminator 30 is then filtered by low pass filter 31 and rectified by waveform rectification circuit 32. A decoder 33 decodes the rectified signal and passes it to display driver 37 which drives display 38, ringer circuit 35 for driving speaker 36, or both. Also provided is a read only memory 34 which contains data and instructions used by the medical data receiver 20.

As set forth above, this description of the medical data receiver and the parameters set forth therein exemplify one suitable receiver. Numerous other receivers and the parameters attendant therewith are suitable for use in this invention.

In operation, a life support system 100 is connected to a living organism. The operation of the medical data reporting system will be set forth with regard to an artificial heart driver/monitor as the life support system 100. However, it should be noted that other life support systems or other medical monitoring devices can be substituted for the artificial heart driver/monitor and come within the scope and spirit of this invention.

As an example, an artificial heart driver/monitor suitable for use with this invention is described in Japanese Patent Application No. 1-82043 (1989). It pumps an artificial heart connected to a living organism. In addition, it monitors the cessation of blood flow during switching between periods of return and transmission of blood, pressure of the suction/transmission blood sack of the artificial heart, contraction/expansion strokes, and other operations and characteristics of the heart. In the event of any irregularities in these operations and characteristics, an alarm will sound.

In a first aspect of the invention, the medical data transmitter 10 periodically requests medical data from artificial heart driver/monitor 100. The interval of time between requests will be designated as $T_s$. The medical data transmitter 10 sends out medical data at specific intervals ($T_r$), where $T_s < T_r$, to the remote location where it is to be monitored. The interval $T_r$ may be selected via keyboard 13. If $T_r$ is not so selected, a previously determined default value will be used. The medical data transmitter transmits the data over a public telephone network 40 to a first telephone number. The public telephone network 40, in response to the dialing of the first telephone number, transmits data to remotely located receiver 20. Medical data receiver 20, located at that remote point, then displays the data. Thus, the invention makes it possible for personnel to monitor the artificial heart driver at locations remote from the heart driver itself.

In a further aspect of the invention, a medical data reporting system in accordance with the first aspect is provided, and additionally, an irregularity detection system is implemented. The medical data transmitter detects whether certain biological functions, such as BFR when life support system 100 is an artificial heart driver/monitor, are within a predetermined range. Any irregularity is reported audibly and visually to the monitoring personnel via the telephone network 40 and remote medical data receiver 20.

For example, when the artificial heart driver/monitor 100 receives a request for medical data, it sends data on the amount of blood being pumped, the blood flow rate (BFR). The BFR, which is indicated by this data, is compared with the prescribed minimum value for BFR, $BFR_1$. The minimum prescribed BFR is indicated by the voltage across the potentiometer 14. The BFR is also compared with $BFR_2$, the maximum prescribed value of BFR as indicated by the potentiometer 15. If the blood flow rate (BFR) is less than the minimum value or greater than the maximum value, a data frame consisting of reporting codes will be created.

Twelve codes are used in this example where the life support system 100 is the artificial heart driver/monitor disclosed in JP1/82043 (1989). However, the number of codes may be varied as needed to display information required for a particular implementation. In this example, the twelve codes will indicate the time, the blood flow rate, and an irregularity indicating code. Depending on the characteristics being monitored, different numbers of codes representing different measured quantities may be used.

The frames will be created once every predetermined interval, the interval designated as $T_e$, which is longer than $T_s$ and $T_r$. Interval $T_e$ may also be selected via keyboard 13. As with $T_r$, if no value is chosen, an internal default value is used. Automatic dialer 17, modem 18, and circuit controller 19 will transmit the dataframe to the public telephone network 40 so that it will be dispatched to a second telephone number.

The public telephone network 40, in response to the dialing of the second telephone number, transmits data to remote receiver 20. Medical data receiver 20, remotely located from the life support system, then displays that data and activates an audible alarm through ringer circuit 35 and speaker 36. Thus, personnel monitoring the artificial heart driver may do so at locations remote from the heart driver itself and be immediately informed of any irregularities.

Figure 3:
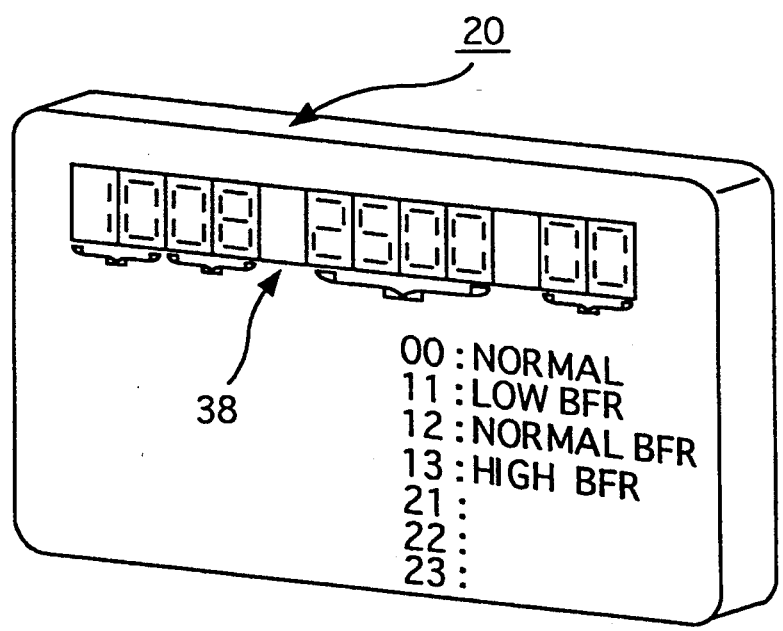
FIG. 3 is a diagram showing a receiver, including its display, in accordance with the invention.

The example reporting frame, discussed above, consists of twelve codes. Typical display of the codes is illustrated in FIG. 3. The first four codes are composed of two codes to display hours and two codes to display minutes, which are used to indicate the current time. The next code is a code that indicates a space (blank). The four codes after that are a four-digit figure to indicate the blood flow rate (BFR). The next code is a code that indicates a space (blank). The final two codes indicate irregularities. When conditions are normal, both irregularity codes will be zero. The transmission of a normal reporting frame will cause figures, such as those indicated in FIG. 3, to be displayed on the display 38 of the medical data receiver 20.

As illustrated in FIG. 3, legends identifying the display elements can be set forth adjacent the appropriate numerals in the display 38. The legends may be printed on a label. For example, under the legend for the two codes which indicate irregularities is a listing of both normal and irregular codes and what they represent. As an example, the display in FIG. 3 indicates that the blood flow rate at 10:08 is 2500 and normal.

An example of the medical data receiver 20 is the Nippon Telephone & Telegraph (NTT) pocket pager. An example of the public telephone network 40 is NTT's pocket pager service network. The public telephone network stores both the telephone number to which the information is to be dispatched and the dataframe to be transmitted in register 44 of public telephone network 40. A coder 46 is activated to transmit the data to remote receiver unit 20.

Written into the read only memory (ROM) 34 of the medical receiver 20 is data that activates the speaker 35 and latches the received dataframe to the display driver 37 when data indicating that the second telephone number was dialed, i.e., that an irregularity exists, is received by the medical data receiver 20. In contrast, when a call is dispatched to the first telephone number i.e., no irregularity exists, a new dataframe is latched onto the display driver 37 but the speaker 36 is not activated. Although the speaker is not activated when data is received indicating that the first number was dialed, the dataframe is latched onto the display driver 37. Subsequently, when the decoder 33 in medical data receiver 20 receives a call dispatched to the second telephone number, a new dataframe is latched onto the display driver 37 and the speaker 36 is activated to ring a prescribed number of times.

The operation of the invention will now be described in detail. When the medical data transmitter 10 is activated, the operator will input at keyboard 13 a regular transmission interval and a transmission interval to be used when there are irregularities ($T_e$), such that ($T_s < T_e < T_r$) for the biological data (BFR in the preferred embodiment). If the user does not enter these values, preprogrammed default values will be used. The minimum allowable value ($BFR_1$) for the biological data that is being monitored is set by potentiometer 14; the maximum allowable value ($BFR_2$) is set by potentiometer 15. To start the operation of the reporting system, the "start" key on the operator's keyboard is activated.

The operation of the medical data transmitter will be described with reference to FIG. 2(a). At step 1, the power is turned on, and the microprocessor is reset. Next, the register, counter, timer, and other internal components are set to their initial values at step 2. Input from the keyboard 13 will then be accepted if anything other than the "start" or "end" keys are pressed (Step 3). Any information input at Step 3 will be inputted to the proper register. To begin operation, the user will press "start". At Step 4, it is determined if the "start" key has been pressed. If so, operation continues to Step 5. If the start key has not been pressed, control will return to Step 3 to await additional input.

At initialization (Step 2), a basic cycle of ten (10) minutes will be written into the regular cycle register ($T_r$) and a basic cycle of one (1) minute will be written into the irregular cycle register ($T_e$). If there should be input of regular cycle data, i.e., a period other than 10 minutes from the keyboard (13), that information will be written into the regular cycle register ($T_r$). If there should be input of irregular cycle data, i.e., a period of other than one minute, that information will be written into the irregular cycle data register ($T_e$).

The default parameters for $T_r$ and $T_e$ are selected to give timely but not unnecessary updates. $T_e$ is set to be much shorter than $T_r$ because, during a period of irregularity, more frequent updates are necessary. These default values are for example only, and may be set as required for a given implementation.

As soon as "start" is input from keyboard 13, the timer will be started with the regular cycle register ($T_r$) as its time limit (Step 5). At this point, the communications may be interrupted by an emergency situation as detected by the driver/monitor 100. This alarm interruption process will be discussed in detail later. The driver/monitor 100 for the artificial heart will be requested to transfer data on blood flow rate (BFR), and that information will be received from the driver/monitor 100 (Step 6). The signals (voltages) that indicate the minimum blood flow rate ($BFR_1$) and the maximum blood flow rate ($BFR_2$) from the potentiometers (14) and (15), respectively, are converted into digital values and read by the microprocessor (Steps 7 and 8).

The data on the blood flow rate (BFR) from the driver/monitor 100 is compared with the minimum value ($BFR_1$) (Step 9), and with the maximum value ($BFR_2$) (Step 10). If the results of the comparison are $BFR_1 < BFR < BFR_2$, the system will indicate the absence of an irregularity by placing "0" into register "AIF" (Step 11). A normal reporting frame is then created (Step 12), and the system checks to see if the timer 16 has exceeded its limit. If the timer has not exceeded its limit ($T_r$) (Step 13), control will return to Step 6 to take additional input from driver/monitor 100 unless the "end" key has been pressed (Step 15) or the time has exceeded its limit. If the timer has exceeded its limit, then the data frame created will be sent out to the public telephone network 40 by means of the automatic dialer 17, modem 18 and the circuit controller 19. Because there is no irregularity, the data frame will be sent to the first number where it will update the display but will not sound the speaker. The above processes are then repeated according to the flow diagram of FIG. 2(a). Each time timer 16 exceeds its set limit ($T_r$), updated data is transmitted to the receiver 20. The receiver 20 then latches that information to the display driver 37.

Referring again to FIG. 2(a), the process of reporting an irregular condition will be described. Once the data on the blood flow rate from the driver 100 has been compared with the minimum value ($BFR_1$) and the maximum value ($BFR_2$), if the comparison indicates that $BFR_1 > BFR$, the microprocessor 11 will create an irregular reporting frame (Step 17) to indicate a low blood flow rate. The frame will includes the current time, the blood flow rate, and the irregular code "11". The information will be sent the public telephone network 40 to be dispatched to the second telephone number. Should the comparison indicate, however, that $BFR > BFR_2$, then the microprocessor 11 will create irregular reporting frame (Step 17) which will include the current time, the blood flow rate, and the irregular code "13", i.e., the code which indicates high blood flow rate. The medical data transmitter then indicates the existence of an irregular reporting frame by placing a "1" in register AIF (Steps 18 and 19) if it does not already contain a "1". The irregular cycle register then is used as the limit of timer 16 (Step 20).

The reporting frame is then transmitted to the second telephone number (Step 21) over public telephone network 40. When this data reaches receiver 20, the speaker 36 is caused to ring. The decoder 33 allows the speaker 36 to ring at specified intervals. The reporting frame is also displayed on display 38. Thus, if the monitor has the medical data receiver 20 with him, he will know that an irregularity has occurred because of the sound generated and will be able to discern when type of irregularity has occurred by observing the information on the display 38.

After the irregular reporting frame has been transmitted (Step 21), the microprocessor 11 waits to find out if the timer 16 has exceeded its limit, $T_e$ (Step 22). If it has not, the system reads input from the keyboard 13 to determine if the "end" key has been activated (Step 23). This cycle continues until timer 16 exceeds its limit, $T_e$.

When the timer 16 exceeds its limit, $T_e$, the driver/monitor 100 will be requested to transfer data, and, as a result, data on the blood flow rate will be accepted (Step 6). The system will then proceed to check the blood flow rate against the predetermined minimum and maximum values (Steps 9 and 10). Should it not be within the predetermined range, an irregular reporting frame will be created (Step 17) and sent to the second telephone number (Step 21)

When the "end" key on the keyboard 13 is depressed, the microprocessor 11 detects this occurrence. (Steps 14 and 15 or Steps 23 and 24). Pressing the "end" key prevents alarm interruptions (described in detail below) from the driver 100. The system goes into a read mode and waits for the activation of the "start" key.

The alarm interruption process will now be described. The driver/monitor 100 for the artificial heart monitors the amount of blood being transmitted, flow stoppages during switches between return and transmission of blood, the pressure of the suction/transmission blood sack of the artificial heart, the contraction/ expansion strokes, where weight of the heart is centered, and other conditions. When there are any irregularities in this data, an alarm message appears on the CRTs 52 and 53. In addition, according to the second aspect of the invention, irregular data is generated and sent to the medical data transmitter 10. This irregular data breaks into the transmission of other data as it is of such a high priority.

Figure 2B:
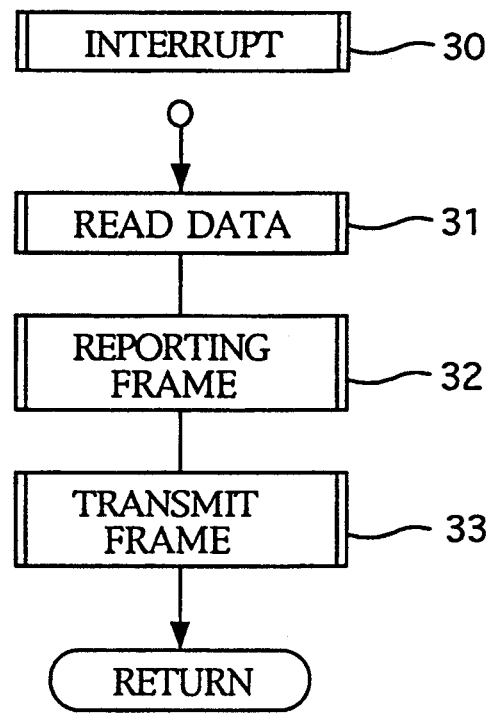

The interruption process is described with reference to FIG. 2(b). When an irregular condition is detected, the microprocessor 11 in medical data transmitter 10 executes an interruption in communications (Step 30) The microprocessor 11 then receives the irregular data from the driver/monitor 100 of the artificial heart (Step 31). That information is converted into codes, as described above. Examples of the meaning of the irregularity codes are shown in FIG. 3 underneath the final two digits of the display. A dataframe is then created (Step 32) that consists in the preferred data transmitter of twelve codes, namely, the current time, the blood flow rate, and the irregularity code. The dataframe then is transmitted (Step 33) over public telephone network 40 to the second telephone number. When the medical data receiver 20 receives this information, the speaker 36 is activated, and the codes for the data frame are indicated on the display 38. Therefore, when the driver/monitor 100 of the artificial heart has itself acknowledged an irregularity regarding the functioning of the artificial heart, that information is transmitted automatically to the medical data transmitter 10 and then sent on to the medical data receiver 20. The irregularities the driver/monitor 100 has discerned then are displayed by the receiver 20, and the user is informed of its presence by an alarm.

In the above embodiment, the receiver 20 discerns between calls to the first and second telephone numbers. For example, the transmitter reacts to an irregularity by dispatching data to a second telephone number. The receiver 20 responds to the transmission of data to the second number by sounding an alarm in addition to the display of information. When conditions are normal, there is only an update of the character display without the sounding of an alarm. That is, information is sent to the first telephone number.

By the use of this invention, trained personnel may monitor the condition of an organism on life support by carrying a remote receiver. They are not required to remain at the site of the life support system 100. When there are irregularities, an alarm will sound to notify the monitoring person of the irregularity.

In the above preferred embodiments, data on the transmission of blood from a driver/monitor 100 of an artificial heart is monitored. However, the invention is not limited to that particular use. The invention can be used in a similar manner for remote monitoring of other data, including respiration cycles, heart beat, electrocardiograms, blood pressure, and body temperature of an organism. The invention can also be used with other life support or monitoring systems.

If the apparatus is housed in a mobile unit (such as a paramedic van, an ambulance, or a rescue helicopter), the medical data transmitter 10 will be equipped with a radio transmitting device to transmit data to a public telephone network. Thus, the transmitter section can be located in a mobile unit and provide information to a remote location in accordance with this invention.

Although the invention has been described with reference to specific embodiments, many other variations and modification are possible while still falling within the spirit and scope of the invention, which is limited only by the claims.

I claim:

1. A medical data reporter for reporting medical data to a remote location comprising:

a medical data transmitter for receiving medical data from a medical monitoring device which measures at least one biological function of an organism associated therewith, and for transmitting the medical data to a telephone network, said medical data transmitter including transmitting means for transmitting the medical data to one of a plurality of phone numbers associated with said telephone network and selecting means for selecting one of said plurality of phone numbers for the transmission of said medical data, wherein said selecting means selects a first telephone number for the transmission of data when it detects no irregularities in the biological functions monitored by said monitoring device and selects a second telephone number for the transmission of data when it detects an irregularity in one or more of the biological functions monitored by said monitoring device; and a medical data receiver located remotely from said medical data transmitter for receiving said medical data from said telephone network and providing said data to a user of said medical data receiver, said medical data receiver displaying said medical data in response to the transmission of data to said first telephone number by said medical data transmitter and said medical data receiver displaying said medical data and emitting an audible sound in response to the transmission of data to said second telephone number.

2. A medical data reporter according to claim 1 wherein an irregularity in a biological function may be detected either by said medical data transmitter or by said medical monitoring device.

3. A medical data reporter according to claim 1 wherein said medical data receiver includes an antenna for receiving said medical data from said telephone network.

4. A medical data reporter according to claim 1 wherein said medical data receiver receives said medical data by means of electromagnetic waves.

5. A medical data reporter according to claim 1 wherein said medical data receiver is a pocket pager, and said telephone network comprises a pocket pager network.

6. The medical data reporter according to claim 1, wherein the medical data transmitter transmits medical data at a predetermined interval of time to the first telephone number when no irregularities are detected in the biological functions monitored by the monitoring device, the medical data receiver displaying medical data including data indicating when the last transmission of medical data occurred.

7. A method of reporting medical data from a medical monitoring device to a remote location comprising:
reading medical data from said medical monitoring device;
transmitting said medical data to a telephone network, wherein said transmitting step further includes the steps of determining if said medical data is within a predetermined range of acceptable values, transmitting said medical data to a first telephone number associated with said telephone network if the medical data is within said predetermined range, and transmitting said medical data to a second telephone number associated with said telephone network if the medical data is not within said predetermined range;
receiving said medical data from said telephone network at said remote location; and
displaying said medical data at said remote location, wherein said step of displaying said medical data further includes the step of producing an audible sound at said remote location if the medical data is transmitted to said second telephone number.

8. The method of reporting medical data according to claim 7, further comprising the steps of transmitting medical data at a predetermined interval of time to the first telephone number when the medical data is within the predetermined range, and displaying the medical data so that data indicating when the last transmission of medical data occurred is displayed.

9. A method of reporting medical data from a medical monitoring device to a remote location, the medical monitoring device measuring at least one biological function of an organism associated therewith, said method comprising:
reading data from said medical monitoring device;
transmitting said data to a telephone network, wherein said transmitting step further includes the step of determining if said monitoring device is indicating an irregularity in the biological functions monitored by said monitoring device, transmitting said medical data to a first telephone number associated with said telephone network if the monitoring device is not indicating an irregularity in the monitored biological functions, and transmitting said medical data to a second telephone number associated with said telephone network if the monitoring device is indicating an irregularity in the monitored biological functions;
receiving said medical data from said telephone network at said remote location; and
displaying said medical data at said remote location, wherein said step of displaying said medical data further includes the step of producing an audible sound at said remote location if the medical data is transmitted to said second telephone number.

10. A method according to claim 9 further including the step of interrupting the transmission of said medical data if the medical monitoring device is reporting any irregularities, and then transmitting data on said irregularities to said second telephone number.

11. The method of reporting medical data from a medical monitoring device according to claim 9, further comprising the steps of transmitting medical data at a predetermined interval of time to the first telephone number when no irregularity in the monitored biological function is not indicated by the monitoring device, and displaying the medical data so that data indicating when the last transmission of medical data occurred is displayed.

* * * * *